US008553832B2

(12) United States Patent
Camus et al.

(10) Patent No.: US 8,553,832 B2
(45) Date of Patent: Oct. 8, 2013

(54) DEVICE FOR OBTAINING PERFUSION IMAGES

(75) Inventors: Estelle Camus, Erlangen (DE); Thomas Redel, Poxdorf (DE); Martin Ostermeier, Buckenhof (DE); Oliver Meissner, München (DE)

(73) Assignee: Siemens Aktiengesellschaft, München (DE)

( * ) Notice: Subject to any disclaimer, the term of this patent is extended or adjusted under 35 U.S.C. 154(b) by 1404 days.

(21) Appl. No.: 11/804,903

(22) Filed: May 21, 2007

(65) Prior Publication Data

US 2008/0292049 A1    Nov. 27, 2008

(51) Int. Cl.
*A61B 6/00* (2006.01)
(52) U.S. Cl.
USPC .............. 378/8; 600/425; 600/431; 600/407; 378/4; 382/128; 382/130; 382/131; 382/132
(58) Field of Classification Search
USPC ......... 600/407, 425, 431; 378/4, 8; 382/128, 382/130, 131, 132
See application file for complete search history.

(56) References Cited

U.S. PATENT DOCUMENTS

| 7,399,220 B2 * | 7/2008 | Kriesel et al. ............. 452/157 |
| 7,729,525 B2 * | 6/2010 | Camus et al. ............. 382/130 |
| 7,840,255 B2 * | 11/2010 | Ichihara ................... 600/425 |
| 7,860,288 B2 * | 12/2010 | Bernhardt et al. ......... 382/128 |
| 2004/0059213 A1 * | 3/2004 | Kassai et al. ............. 600/410 |
| 2004/0077952 A1 * | 4/2004 | Rafter et al. ............. 600/481 |
| 2006/0120507 A1 | 6/2006 | Brunner et al. ............ 378/62 |
| 2006/0239528 A1 | 10/2006 | Camus et al. ............. 382/128 |
| 2007/0031018 A1 | 2/2007 | Camus et al. ............. 382/130 |
| 2007/0041625 A1 | 2/2007 | Camus et al. ............. 382/130 |
| 2008/0033285 A1 * | 2/2008 | Camus et al. ............. 600/425 |
| 2010/0272344 A1 * | 10/2010 | Ichihara et al. ............ 382/132 |
| 2012/0041299 A1 * | 2/2012 | Kassai et al. ............. 600/413 |

* cited by examiner

*Primary Examiner* — Unsu Jung
*Assistant Examiner* — Amanda Lauritzen
(74) *Attorney, Agent, or Firm* — Lempia Summerfield Katz LLC (57) ABSTRACT

A system and method for obtaining perfusion images is disclosed. The system and method includes hardware and software for determining physiological characteristics of a patient and determining imaging parameter values for an imaging modality based on the patient's physiological characteristics. The system also includes a controller operative to receive the imaging parameter values for controlling an X-ray device. The X-ray device is coupled with the controller and acquires projection images of the patient, and outputs the projection images to a perfusion evaluation computer for evaluating the perfusion of an region of interest represented in the projection images. The perfusion rate of the region of interest is then output to an output device, such as a display or printer.

28 Claims, 8 Drawing Sheets

DEVICE FOR OBTAINING PERFUSION IMAGES

TECHNICAL FIELD

The present embodiments relate to a system and method for obtaining perfusion images. In particular, the present invention relates to a system and method for measuring a patient's physiological characteristics, and using the measured patient's physiological characteristics to compute one or more imaging parameter values for one or more imaging modalities.

BACKGROUND

The steps in planning for the treatment of blood vessels, such as brain vessels and coronary that have been altered by atherosclerosis, include the angiographic display of those blood vessels and, the quantitative calculation of the diameter, number and length of a stenosis or blockage. Besides morphological statements, such as directly visualizing a stenosis, imaging parameter values of imaging modalities are gaining increasing importance, such as for visualizing parenchymal perfusion distally of the stenosis in the event of a stroke.

Perfusion, which is the circulation of blood through tissue, is one indicator used for diagnosing an region of interest in a patient affected by a stenosis or blockage. By determining perfusion at the capillary level of the region of interest, the effect of the stenosis or blockage of an artery can be assessed and localized directly. The extent of the stenosis or blockage can also be determined. From this information, a therapeutic treatment can be planned, and its success can then be monitored immediately after the intervention by determining the perfusion of the region of interest.

Currently, there are some established perfusion imaging modalities, including positron emission tomography ("PET"), single photon emission computed tomography ("SPECT"), magnetic resonance tomography ("MRT"), or ultrasound reinforced with contrast agent. These imaging modalities offer the ability of quantifying the perfusion status of an region of interest of a patient, such as the parenchyma/myocardium. In general, these imaging modalities can be performed in cases of stable angina pectoris, chronic total blockages, or for risk stratification after a myocardial infarction or when a stroke has occurred.

In principle, the degree of perfusion of the myocardium or the parenchyma supplied by an artery can also be obtained from the data of projection-based and angiographic computed tomography. Analyzing perfusion using projection-based techniques allows for the determination of an intervention's success, and may permit supplementing or changing the therapeutic treatment in the same session.

A general principle for ascertaining the perfusion status of a patient's region of interest, such as the patient's myocardium, using an angiographic X-ray device (cardiac perfusion assessment or "TIMI blush") is described in U.S. Pat. App. Pub. No. 2007/0041625, which is incorporated by reference herein, and U.S. Pat. App. Pub. No. 2007/0031018, which is incorporated by reference herein.

In general, contrast agent injection is done arterially into an region of interest, and is often done directly into an affected vessel. When the region of interest is captured, the amount of the contrast agent bolus present in the region of interest is often used to determine the perfusion of the region of interest. However, current systems for determining perfusion of a region of interest in a patient use fixed, predefined recording protocols.

BRIEF SUMMARY

A system and method for obtaining perfusion images is disclosed herein. The system includes a computer operative to determine one or more physiological characteristics of a patient. The system also includes another computer that receives one or more determined physiological characteristics and uses them to compute one or more imaging parameter values of one or more imaging modalities. The system further includes an X-ray device that acquires one or more projection images, such as by using angiography, representative of an region of interest of the patient using the imaging modality. Additionally, the system has a perfusion evaluation computer that determines a perfusion rate of the region of interest based on the one or more acquired projection images. One or more output devices included in the system are configured to store and display data produced by the system, including the determined physiological characteristics, the determined imaging parameter values, the one or more acquired projection images, and the perfusion rate of the region of interest determined by the perfusion evaluation computer.

The method includes measuring one or more physiological characteristics of a patient and determining one or more imaging parameter values of one or more imaging modalities using the one or more physiological characteristics. The method also includes acquiring one or more projection images representative of an region of interest of the patient using one or more imaging modalities. Furthermore, the method encompasses determining a perfusion rate of the region of interest based on the one or more acquired projection images and, finally, outputting the acquired data, such as by storing perfusion rate of the region of interest or by displaying the one or more acquired projection images.

DETAILED DESCRIPTION

To clarify the use in the pending claims and to hereby provide notice to the public, the phrases "at least one of <A>, <B>, . . . and <N>" or "at least one of <A>, <B>, . . . <N>, or combinations thereof" are defined by the Applicant in the broadest sense, superseding any other implied definitions herebefore or hereinafter unless expressly asserted by the Applicant to the contrary, to mean one or more elements selected from the group comprising A, B, . . . and N, that is to say, any combination of one or more of the elements A, B, . . . or N including any one element alone or in combination with one or more of the other elements which may also include, in combination, additional elements not listed.

Figure 1:
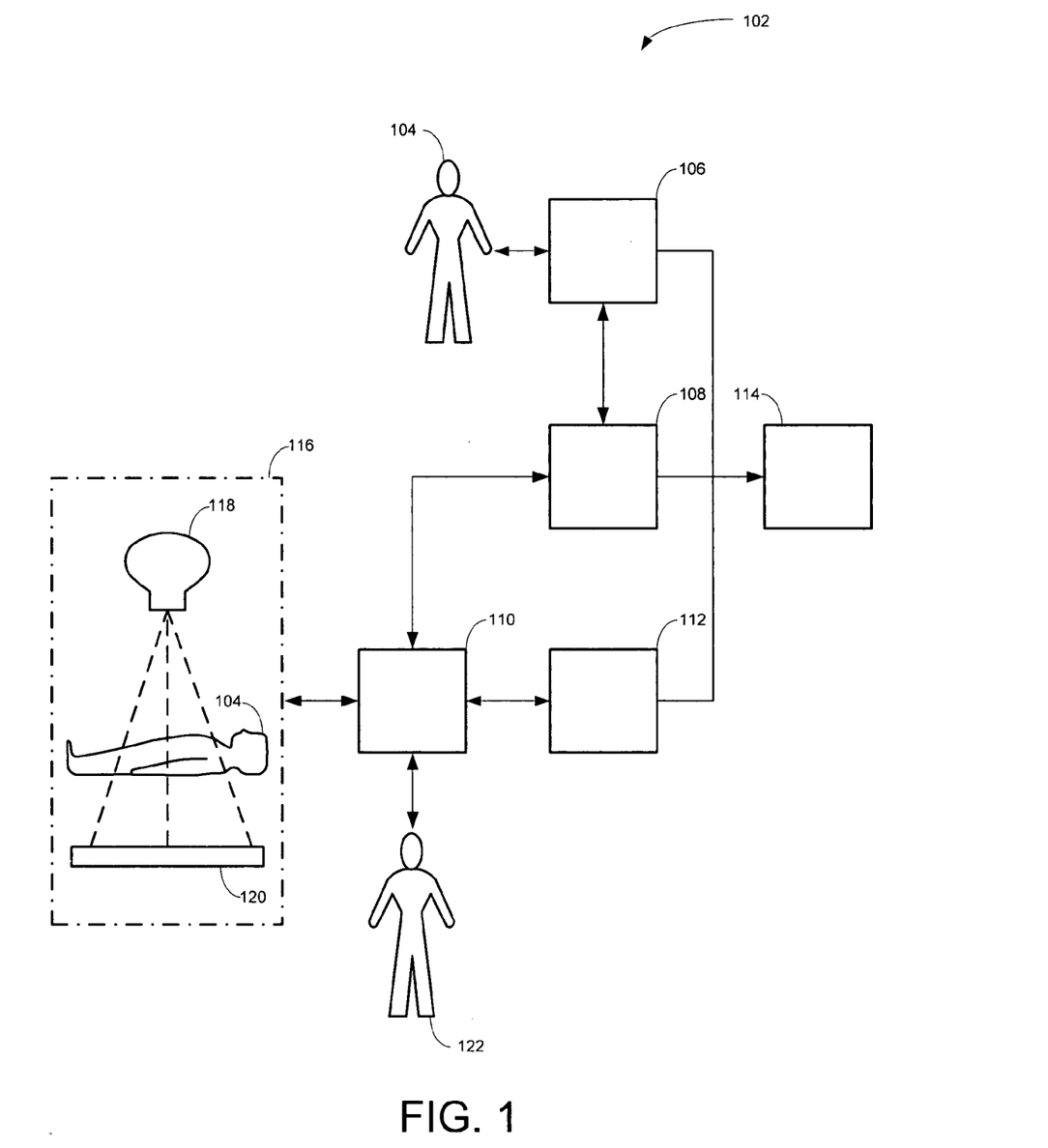
FIG. 1 is a block diagram of one example of a system used to obtain perfusion images based on one or more measured physiological characteristics of a patient.

FIG. 1 is a block diagram of one example of a system 102 used to obtain perfusion images based on one or more measured physiological characteristics of a patient 104. The system 102 includes a computer 106 for measuring one or more physiological characteristics of a patient 104 coupled with a computer 108 operative to compute imaging parameter values of a selected imaging modality based on the one or more measured physiological characteristics. The system 102 also includes a controller 110 operative to control an X-ray device 116, and the controller 110 is coupled with the computer 108 and a perfusion evaluation computer 112. The computer 106, the computer 108, the controller 110, the perfusion evaluation computer 112, or combinations thereof, are further coupled with an output device 114 for outputting data. A user 122 interacts with the system 102 using the computer 106, the computer 108, the controller 110, the perfusion evaluation computer 112, or combinations thereof. As shown in FIG. 1, the user 122 interacts with the system 102 using the controller 110. However, the user 122 could interact with the system 102 using the computer 106 or other devices.

In one embodiment, the computer 106, the computer 108, the controller 110, the perfusion computer 112, the output device 114, or combinations thereof are each separate devices. In an alternative embodiment, the computer 106, the computer 108, the controller 110, the perfusion evaluation computer 112, the output device 114, or combinations thereof, are the same device even when listed separately. The devices shown in the system 102 may be connected via a wired connection, a wireless connection, or combinations thereof. The devices shown may be in the same geographic location, different geographic locations, or combinations thereof. It is also possible that each of the devices are implemented in software, hardware, or combinations thereof.

The computer 106 is operative to measure one or more physiological characteristics of a patient 104. In general, a physiological characteristic is a measurable or non-measurable physiological condition of a patient 104. Examples of physiological characteristics include, but are not limited to, cardiac output, coronary flow reserve, fractional flow reserve, heart rate, blood pressure, age, weight, race, sex, any other characteristic describing a patient 104, any other now known or later learned physiological characteristics, or combinations thereof. In one embodiment, the computer 106 computes one or more physiological characteristics of a patient 104 using a parameter-based analysis, such as by receiving a predefined volumetric dataset describing region of interest of the patient 104. In another embodiment, the computer 106 computes one or more physiological characteristics of a patient 104 using a direct measurement, such as by measuring the timing of a contrast bolus injected into the patient 104. The computer 106 can also be configured to receive input from the user 122, the patient 104, or combinations thereof. For example, the user 122 could record the age of the patient 104, the weight of the patient 104, the sex of the patient 104, any other input describing the patient 104, or combinations thereof, into the computer 106 using an input device (not shown) coupled thereto.

As discussed above, in one embodiment, the computer 106 determines one or more physiological characteristics of a patient 104 using a parameter-based analysis. An example of a computer 106 that determines one or more physiological characteristics of a patient 104 using a parameter-based analysis is described in U.S. Pat. App. Pub. 2006/0239528, which is incorporated by reference herein. In one embodiment of a parameter-based analysis, the computer 106 receives a dataset describing a region of interest of a patient 104, such as a dataset describing the patient's 104 vascular system in three-dimensions. The dataset describing the region of interest could be pre-specified to the computer 106, such as on a computer-readable medium, or the dataset could be entered in by the user 122, the patient 104, or combinations thereof, using an input device (not shown) coupled with the computer 106. In another alternative, the dataset could be acquired using the X-ray device 116, or one or more imaging devices, using an imaging modality, such as angiographic computed tomography that generates volumetric datasets of a region of interest in the patient 104.

Using the dataset, the computer 106 is then able to compute the blood flow velocity of the region of interest described by the dataset. In one embodiment, the computer 106 is operative to measure the blood flow velocity of the circulatory system of the patient 104. Alternatively, the computer 106 is operative to measure the blood flow velocity of the pulmonary circulation of the patient 104. In addition to the circulatory and pulmonary systems, other regions of interest include, but are not limited to, the myocardium, the gastrointestinal tract, other anatomical structures or systems, or combinations thereof.

Alternatively, or in addition to, using a dataset describing a region of interest in the patient 104 to compute one or more physiological characteristics, the computer 106 could also use an electrocardiogram, a spirometer, an electronic blood pressure monitor, any other now known or later developed patient monitoring devices, or combinations thereof, to compute one or more physiological characteristics of the patient 104. In this embodiment, the patient monitoring device may be coupled to the computer 106, the computer 108, the perfusion evaluation computer 112, the controller 110, the output device 114, the X-ray device 116, or combinations thereof. The data acquired by the patient monitoring device, such as the blood pressure of the patient 104 over a period of predetermined time, is then used as input to the computer 106 for calculating one or more physiological characteristics of the patient 104.

In another embodiment, the computer 106 computes one or more physiological measurements of a patient 104 by direct physiological measurement. In general, direct physiological measurement includes performing one or more examinations on the patient 104 to determine one or more physiological characteristics. For example, direct physiological measurement may include injecting the patient 104 with a test bolus. As disclosed herein, it should understood that the region of interest injected with the test bolus may be the same as, or different from, the region of interest where a stenosis or blockage may be located. After injecting the test bolus, the computer 106 then monitors the movement of the test bolus through the injected region of interest in the patient 104 to compute one or more physiological characteristics of the patient 104. Monitoring the injected region of interest of the patient 104 could also be done by one or more devices coupled with the computer 106, such as the perfusion evaluation computer 112, the user 122, or combinations thereof.

In one embodiment, monitoring of the test bolus provides information relating to the integrated flow behavior of the patient 104. For example, monitoring the test bolus movement through the injected region of interest provides information relating to the blood flow velocity of the injected region of interest. In one embodiment, the computer 106 is configured to monitor the speed at which the test bolus passes through the injected region of interest. In this embodiment, the X-ray device 116 is configured to acquire one or more projection images of the injected region of interest and, based on the time taken for the test bolus to perfuse the injected region of interest from the recorded images, the relative speed of the patient's 104 blood flow velocity is determined. Determining the speed at which the test bolus passes through the injected region of interest may also include the use of one or more components in the system 102 other than the computer 106 and the imaging device 116, such as the controller 110, the computer 108, the perfusion evaluation computer 112, or combinations thereof. The results of monitoring the test bolus could also be output to the output device 114 coupled with the computer 106.

In another embodiment, monitoring of the test bolus includes an evaluation of Thrombolysis in Myocardial Infarction ("TIMI") flow grades of the injected region of interest. In general, the evaluation of TIMI flow grades are used for the assessment of coronary artery flow in acute coronary syndromes. However, the evaluation of TIMI flow grades can also be done on other injected areas of interest, including, but not limited to, the circulatory system, the pulmonary system, the gastrointestinal tract, the myocardium, other anatomical structures or systems, or combinations thereof. TIMI flow grades include a range from 0-3, where 0 represents a complete occlusion of the infarct-related artery; 1 represents some penetration of a contrast agent material beyond an obstruction but without perfusion of a distal coronary bed; 2 represents perfusion of the entire infarct vessel into the distal coronary bed, but with delayed flow compared with a normal artery; and 3 represents a full perfusion of the infarct vessel with normal blood flow. The evaluation of the TIMI flow grades may be done by the user 122, by one or more components of the system 102, such as the perfusion evaluation computer 112, by an external device coupled with the system 102, or combinations thereof. The evaluated TIMI flow grades of the injected region of interest may then be used to generate a time attenuation curve of the injected region of interest.

Alternatively, a time attenuation curve of the injected region of interest may be calculated based on the brightness of the contrast as viewed from one or more projection images representative of the injected region of interest. In this embodiment, the computer 106 communicates with the X-ray device 116 to acquire one or more projection images of the injected region of interest. The computer 106 then examines the same pixel from the set of acquired projection images, and by examining the brightness of the pixel as it changes over time due to the flow of the contrast through the injected region of interest, the computer 106 can plot and store data representative of the brightness of the pixel as a function of time. Thus, a substantially white or bright pixel would indicate a lack of contrast and a darker or substantially black pixel would indicate the presence of contrast. Accordingly, similar to the manner in which the change of TIMI flow grades assigned to the injected region of interest can be used to plot the time attenuation curve of the injected region of interest, so can the change in brightness of the selected pixel be used to plot a time attenuation curve of the injected region of interest. Using the time attenuation curve, the computer 106 can further determine the blood flow velocity of the injected region of interest, such as by taking the derivative of the time attenuation curve. The blood flow velocity derived from the time attenuation curve or the data used in generating the time attenuation curve is further accessible by one or more devices in the system 102.

The computer 108 is operative to compute imaging parameter values for one or more imaging modalities based on the one or more measured physiological characteristics. The computer 108 can also compute one or more imaging parameter values for a previously selected imaging modality. In another embodiment, the user 122 can direct the computer 108, such as through an input device (not shown), to compute a selected imaging parameter value for a selected imaging modality. The computer 108 computes the imaging parameter values of one or more imaging modalities based on a parameter-based analysis performed by the computer 106, by the results of a direct physiological measurement performed on the patient 104, or combinations thereof.

The imaging parameter values computed by the computer 108 include, but are not limited to, a time delay, the framerate of the images recorded by the X-ray device 116, the amount of contrast agent to inject into the patient 104, the length of time in which the contrast agent should be injected into the patient 104, the length of time in which projection images are recorded, the number of projection images to be acquired by the X-ray device 116 of the region of interest, any other now known or later developed imaging parameter values, or combinations thereof. In one embodiment, the time delay determined by the computer 108 is a delay between the time in which the patient 104 is injected with a contrast agent and the time in which the X-ray device 116 begins imaging the patient 104.

In one embodiment, the computer 108 implements a look-up table that correlates a predetermined set of values, such as imaging parameter values, with one or more physiological characteristics. Where the computer 108 implements a look-up table, for each physiological characteristic determined or measured by the computer 106, there may be one or more imaging parameter values that correspond to the physiological characteristic. For example, given the patient's 104 blood flow velocity as input, the computer 108 uses the look-up table to calculate the time between the time in which the patient 104 is injected with contrast and the time in which the controller 110 should instruct the X-ray device 116 to begin recording images, and then outputs the computed time delay. The look-up table may also be populated with values that are predetermined by one or more experimental trials based on a population of patients having similar physiological characteristics. In another embodiment, the look-up table is populated with values that are computed based on one or more simulations previously performed.

In yet a further embodiment, the look-up table is modified by the computer 108, by the user 122, or combinations thereof, when the physiological characteristics of the patient 104 do not correlate to one or more imaging parameter values. For example, where the physiological characteristics of the patient 104 do not correlate to one or more imaging parameter values, an output on the output device 114, such as an error message, may prompt the user 122 to enter in one or more imaging parameter values for the one or more physiological characteristics. Alternatively, the computer 108 may derive one or more imaging parameter values corresponding to one or more physiological characteristics based on an approximation of the values previously entered into the look-up table.

In another embodiment, the computer 108 is implemented as an expert system that uses one or more physiological characteristics as input to determine one or more imaging parameter values. In general, an expert system is a computer system, often implemented as a computer program, that contains a stock of rules, a set of particular facts, and a "logical engine" that allows the system to apply the supplied facts to the programmed rules to reach conclusions that can be drawn from them. In this manner, an expert system is often defined as "knowledge-based" system operative to solve problems in one or more disciplines. In one embodiment, the expert system is supplied with facts and rules relating to imaging parameter values and physiological characteristics that allow the expert system to derive one or more imaging parameter values for one or more physiological characteristics entered as input. The expert system may be further configured to communicate with the user 122 via the output device 114, or one or more devices in the system 102, where the expert system requires further information to derive one or more imaging parameter values.

In yet a further embodiment, the computer 108 is implemented as a neural network that uses one or more physiological characteristics as input to determine one or more imaging parameter values. In general, a neural network, or ANN (Artificial Neural Network), is designed to take a pattern of data and generalize from it, much as would the human brain, even if the data is "noisy" or incomplete. It does this in effect by a sophisticated form of trial and error, or in other words, by varying the strengths of connections between individual processing elements (analogous to neurons in the human brain) until the input yields the right output. The neural network may be initially preconfigured with a set of experimentally determined data of one or more imaging parameter values that correlate to one or more physiological characteristics. The neural network may further be configured to augment, supplement, alter, or combinations thereof, the initially preconfigured data when the computer 108 is supplied with one or more physiological characteristics from the computer 106. The neural network may also allow the user 122 to augment, supplement, alter, or combinations thereof, the data representative of the associations between one or more imaging parameter values and one or more physiological characteristics.

Alternatively, or in addition to, computing one or more imaging parameter values from the parameter-based analysis of the computer 106, the computer 108 is also configured to compute the one or more imaging parameter values from the results of the direct physiological measurement performed on the patient 104. As the data representative of the time attenuation curve calculated by the computer 106 is accessible by the computer 106, the time attenuation curve can be manipulated by the computer 108 to determine one or more imaging parameter values, such as through the use of the look-up table, the expert system, the neural network, or combinations thereof. For example, as the time attenuation curve is representative of the change in perfusion of an injected region of interest over time due to the introduction of a contrast agent, the computer 108 can use the time attenuation curve to determine the amount of contrast agent required to perfuse the injected region of interest. Additional information the computer 108 can derive from the time attenuation curve includes, but is not limited to, the minimum amount of contrast to inject for perfusion to occur, the maximum amount of contrast for perfusion to occur, the time taken for the contrast to perfuse the injected region of interest, the time delay between when perfusion occurs and when the contrast was first injected, any other information derivable from the time attenuation curve, or combinations thereof.

The one or more imaging parameter values determined by the computer 108 can be output to the output device 114, such as by being displayed on a monitor, or being printed on a printer. The user 122 can also supplement or alter the imaging parameter values output to the output device 114 by one or more input devices (not shown) coupled with the computer 108. For example, using a keyboard, the user 122 could enter in additional imaging parameter values for one or more imaging modalities.

The controller 110 is coupled with the computer 108 and operative to receive the one or more imaging parameter values from the computer 108. In one embodiment, the controller 110 is implemented as a system controller operative to control the X-ray device 116 as described in U.S. Pat. App. Pub. No. 2006/0120507, which is incorporated by reference herein. When coupled with the computer 108, the controller 110 uses the imaging parameter values received from the computer 108 as the imaging parameter values for one or more selected imaging modalities. Alternatively, or in addition, the controller 110 may use predetermined default imaging parameter values for one or more imaging parameter values where the computer 108 does not provide a complete set of imaging parameter values. By way of simplistic example only, an imaging modality, such as angiographic computed tomography, may require values for three imaging parameters: image quality, framerate, and scene duration. In this example, if the computer 108 determines an image quality value and a framerate value based on one or more physiological characteristics, but does not compute a scene duration value, the controller 110 may use a predetermined default scene duration value. Alternatively, the controller 110 may compute an imaging parameter value not determined by the computer 108, or the user 122 may input one or more imaging parameter values to the controller 110 to supplement, override, or combinations thereof, the imaging parameter values provided by the computer 108, the controller 110, or combinations thereof.

The controller 110 can also receive one or more projection images recorded by the X-ray device 116 and store them on a storage device (not shown) coupled with the controller 110, or the controller 110 can output the one or more projection images on the output device 114. The X-ray device 116 includes an X-ray source 118 and an X-ray detector 120. The patient 104 is positioned between the X-ray source 118 and the X-ray detector 120, such that an region of interest can be captured in one or more projection images. The projection images recorded by the X-ray device 116 may be two-dimensional angiographic images, a set of projection images used to construct a three-dimensional image, or combinations thereof. For example, the X-ray device 116 may be configured to record projection images using traditional angiography. Alternatively, or in addition to traditional angiography, the X-ray device 116 may be configured to record projection images using angiographic computed tomography, whereby a set of projection images are reconstructed into a three-dimensional volumetric image as described in U.S. Pat. App. Pub. 2006/0120507.

The perfusion evaluation computer 112 is coupled with the controller 110 and operative to receive one or more projection images recorded by the X-ray device 116. The perfusion evaluation computer 112 is further operative to evaluate the recorded projection images to determine the amount of perfusion of the region of interest recorded by the X-ray device 116. The perfusion evaluation computer 112 is also configured to compute the perfusion rate of the region of interest. For example, and as described in U.S. Pat. App. Pub. No. 2007/0041625, the perfusion evaluation computer 112 can use a comparison of myocardial blush for a set of acquired projection images to determine the rate of perfusion for an region of interest. Alternatively, the user 122 may be trained to determine the perfusion rate of the region of interest based on assigning TIMI flow grades as previously discussed above. The perfusion rate of the region of interest can also be output to the output device 114 coupled with the perfusion evaluation computer 112.

Figure 2:
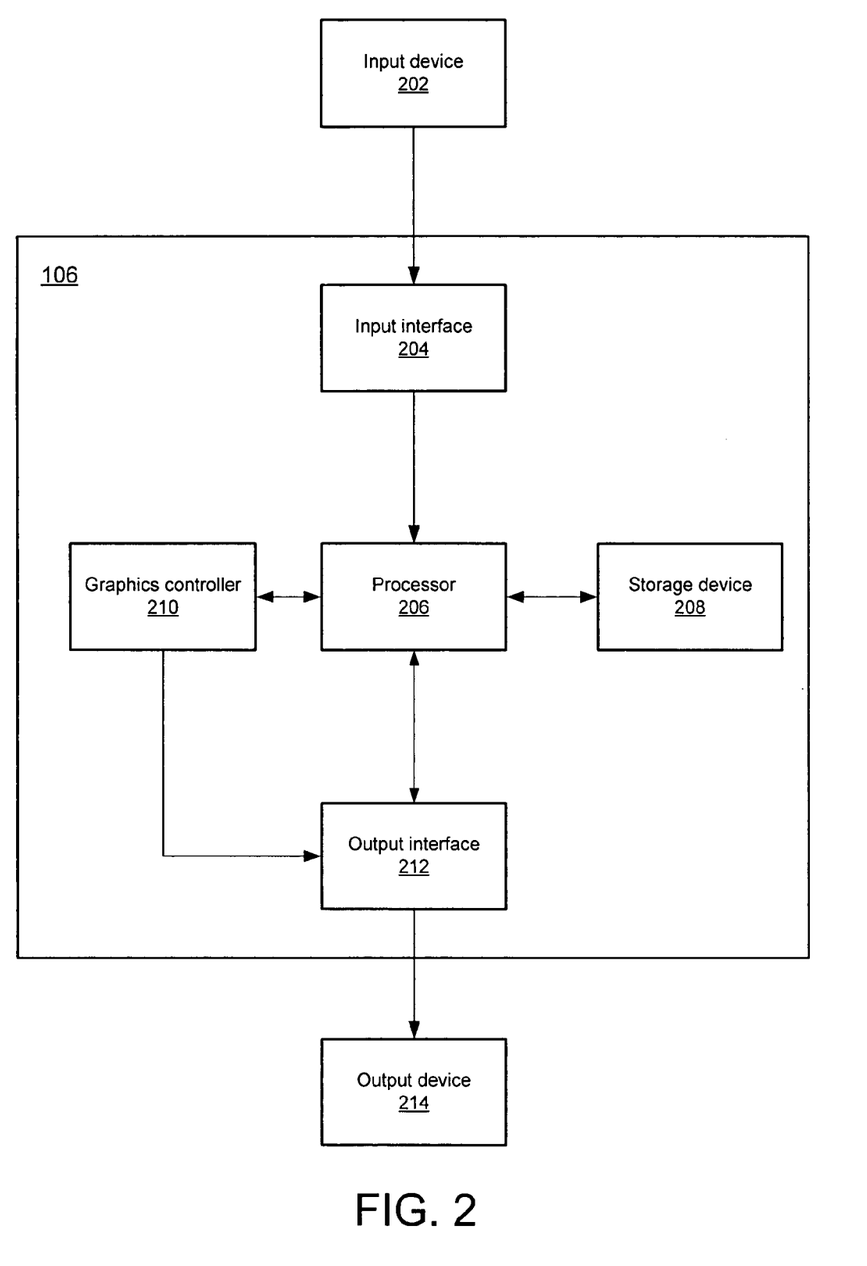
FIG. 2 is a block diagram of one example of a computer used to measure one or more physiological characteristics of a patient.

FIG. 2 is a block diagram of one example of a computer 106 used to measure one or more physiological characteristics of a patient 104. In one embodiment, the computer 106 includes an input device 202 coupled with an input interface 204. The input interface 204 is further coupled with a processor 206. The processor 206 is coupled with a storage device 208, a graphics controller 210, and an output interface 212. The graphics controller 210 is also coupled with the output interface 212. The output interface 212 is further coupled with an output device 214 and can communicate with one or more devices coupled with the processor 206.

With reference to FIG. 1 and FIG. 2, the input device 202 is operative to receive an input from the patient 104, the user 122, one or more devices coupled with the system 102, or combinations thereof. The input device 202 may be an audio input device, a tactile input device, a memory storage device, any now known or later developed input device, or combinations thereof. In one example, the input device 202 is a microphone. In another example, the input device 202 is a keyboard, mouse, trackball, touch pad or other pointer control. In another example, the input device 202 is a memory storage device, such as a hard disk drive, compact disc, digital video disc, flash memory, random access memory, or combinations thereof. In yet another example, the input device 202 is an electrocardiogram, a spirometer, an electronic blood pressure monitor, any other known or later developed patient monitoring device, or combinations thereof.

In one embodiment, the input device 202 is operative to receive input for a parameter-based analysis of one or more physiological characteristics of a patient 104. For example, the input device 202 may be a keyboard where a user 122 inputs one or more physiological characteristics relating to the patient 104 including, but not limited to, heart rate, blood pressure, age, weight, race, or sex. As an alternative example, the input device 202 may be a compact disc that contains a dataset describing an region of interest in the patient 104, such as a dataset describing the patient's 104 vascular system as described in U.S. Pat. App. Pub. 2006/0239528. The input collected by the input device 202 is passed to the input interface 204 for processing by the processor 206.

The input interface 204 coupled with the input device 202 is operative to receive the input collected by the input device 202. The input interface 202 may be a wired interface, such as PS/2, USB, Ethernet, IDE/ATA, SCSI, SATA, or IEEE 1394, a wireless interface, such as 802.11 a/b/g, Bluetooth, RF, infrared, an audio interface, such as stereo, S/PDIF, AES/EBU, or combinations thereof. In one embodiment, the input interface 204 is a PS/2 interface coupled with the input device 202, which is a keyboard. In another embodiment, the input interface 204 is an IDE/ATA interface and the input device 202 is a hard drive. In yet a further embodiment, the input interface 204 is an IDE/ATA interface and the input device 202 is a compact disc. In an alternative embodiment, the input interface 204 is an Ethernet interface, and the input device 202 is the X-ray device 116.

The processor 206 is operative to process the information collected by the input device 202. The processor 206 may be a general processor, a data signal processor, graphics card, graphics chip, personal computer, motherboard, memories, buffers, scan converters, filters, interpolators, field programmable gate array, application-specific integrated circuit, analog circuits, digital circuits, combinations thereof, or any other now known or later developed processor. Alternatively, or in addition, the processor 206 is adapted to implement software written in a computer programming language, such as BASIC, C, Dylan, Euphoria, ASP, C++, Java, Python, PHP, Javascript, any now known or later developed computer programming language, or combinations thereof.

In one embodiment, the processor 206 receives one or more physiological characteristics inputted by the user 122 and communicates with the storage device 208 to store them for later retrieval. In another embodiment, the processor 206 receives data from the input device 202 and calculates one or more physiological characteristics. For example, the processor 206 may contain software for calculating the blood flow velocity of an region of interest in the patient 104 using one or more volumetric datasets entered as input using the input device 202 that describe the region of interest. As another example, the processor 206 may contain software for calculating the cardiac output of the patient 104 using an electrocardiogram as an input device 202. In yet another embodiment, the processor 206 is operative to calculate one or more physiological characteristics of the patient 104 based on a direct physiological measurement. For example, the processor 206 may be operative to evaluate the TIMI flow grades of an region of interest injected with a test bolus, as described in U.S. Pat. App. Pub. 2007/0041625. The processor 206 may further receive input from the X-ray device 116, such as one or more projection images, acting as an input device 202. Other components, such as the controller 110, the perfusion evaluation computer 112, the computer 108, or combinations thereof, may further serve as one or more input devices for the computer 106.

The storage device 208 is operative to store input received from the input device 202, data processed by the processor 206, data processed by the graphics controller 210, or combinations thereof. The storage device 208 may be random access memory, cache memory, dynamic random access memory, static random access memory, flash memory, virtual memory, video memory, magnetic memory, optical memory, any known or later developed memory technology, or combinations thereof. In one embodiment, the storage device 208 is a hard drive. In another embodiment, the memory storage device 208 is a DVD+RW. In a further embodiment, the storage device 208 is a secure digital (SD) card, or other now known or later developed data storage device. The storage device 208 is further operative to allow access to stored data by one or more devices including, but not limited to, the processor 206, the graphics controller 210, the output device 214, one or more devices of the system 102, or combinations thereof.

The graphics controller 210 is operative to control the display of data on the output device 214 coupled with the processor 206. In one embodiment, the graphics controller 210 is operative to control the display of one or more projection images acquired by the X-ray device 116. In another embodiment, the graphics controller 210 is configured to control the display of one or more images representative of an region of interest described by a volumetric dataset processed by the processor 206. The images displayed on the output device 214 may be two-dimensional projection images, or one or more volumetric images representative of one or more two-dimensional projection images. In another embodiment, the graphics controller 210 is operative to control display of one or more physiological characteristics inputted by the input device 202. In one embodiment, the graphics controller 210 is a processor. In another embodiment, the graphics controller 210 is software written in a computer programming language, such as BASIC, C, Dylan, Euphoria, ASP, C++, Java, Python, PHP, Javascript, any now known or later developed computer programming language, or combinations thereof.

The output interface 212 facilitates the output of data by the processor 206, the graphics controller 210, any other device coupled with the processor 306, or combinations thereof to the output device 214. The output interface 212 may be a wired interface, such as PS/2, USB, Ethernet, IDE/ATA, SCSI, SATA, IEEE 1394, VGA, DVI, or HDMI, a wireless interface, such as 802.11 a/b/g/n, Bluetooth, RF, infrared, an audio interface, such as stereo, S/PDIF, AES/EBU, EIAJ optical, or combinations thereof.

The output device 214 outputs data processed by the processor 206, the graphics controller 210, or combinations thereof, communicated through the output interface 212. The data output by the output device 214 may text, graphics, or combinations thereof. The output device 214 may be a display device such as a monitor, CRT, LCD, plasma screen, flat-panel, projector, any other now known or later developed display device, a printing device, such as a laserjet printer, a color printer, any other now known or later developed printing device, a storage device, another computer, or combinations thereof. The output device 214 can also be the output device 114. The output device 214 can also be any other device of the system 102, including, but not limited to, the computer 108, the controller 110, the X-ray device 116, the perfusion evaluation computer 112, the output device 114, or combinations thereof.

The data output by the output device 214 may include one or more physiological characteristics calculated by the processor 206, one or more physiological characteristics input to the input device 202, one or more projection images output by the X-ray device 116, one or more images, two-dimensional or otherwise, representative of an region of interest in the patient 104, or combinations thereof. The output device 214 may also output a user interface allowing the patient 104, the user 122, any other device of the system 102, or combinations thereof, to interact with the computer 106.

Figure 3:
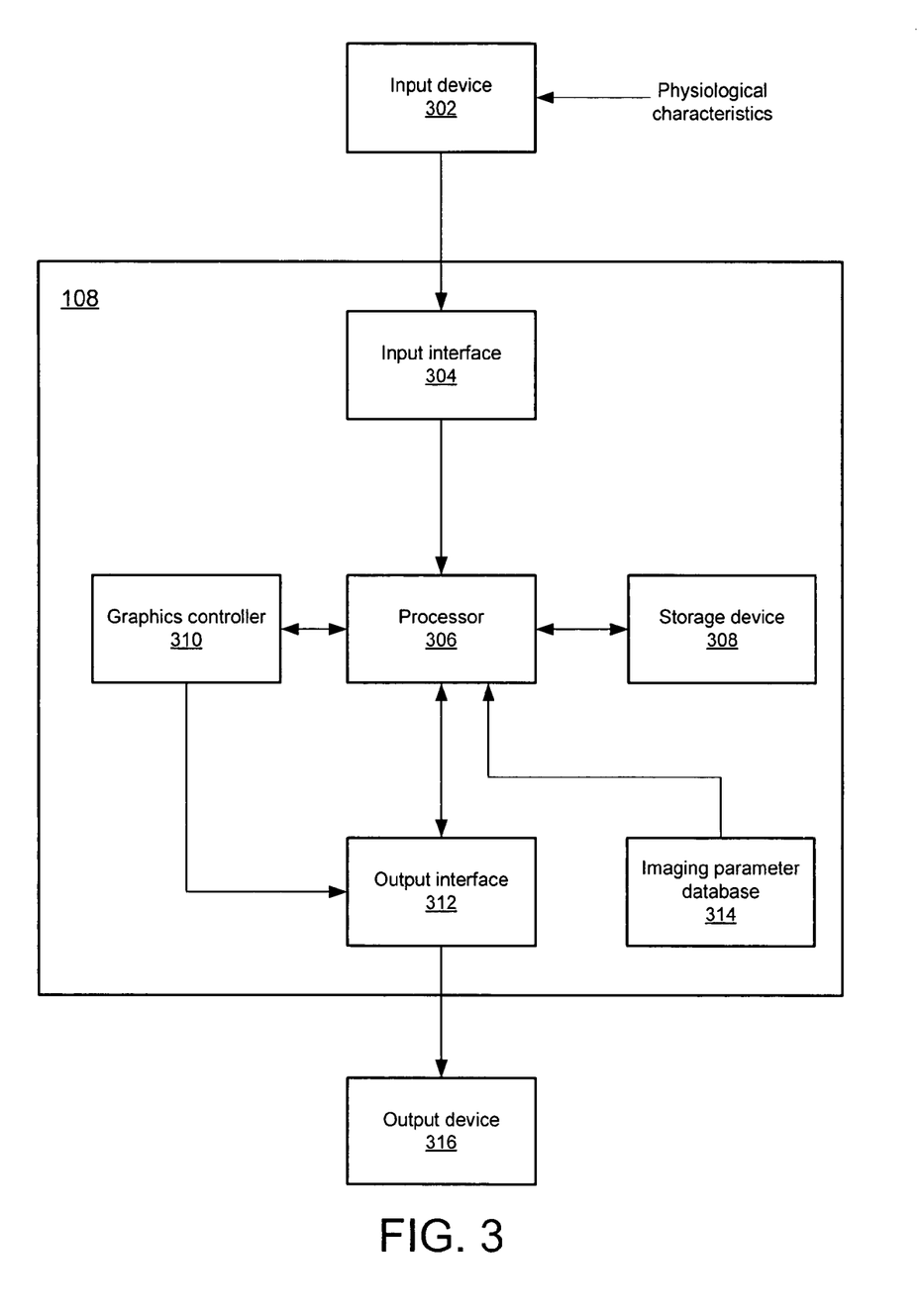
FIG. 3 is block diagram of one example of a computer used to determine one or more imaging parameter values of an imaging modality using the measured one or more physiological characteristics.

FIG. 3 is block diagram of one example of the computer 108 used to determine one or more imaging parameter values of one or more imaging modalities using the one or more physiological characteristics from the computer 106. In one embodiment, the computer 108 includes an input device 302 coupled with an input interface 304. The input interface 304 is further coupled with a processor 306. The processor 306 is coupled with a storage device 308, a graphics controller 310, an imaging parameter database 314, and an output interface 312. The graphics controller 310 is also coupled with the output interface 312. The output interface 312 is further coupled with an output device 314 and can communicate with one or more devices coupled with the processor 306.

With reference to FIG. 1 and FIG. 3, the input device 302 is operative to receive an input from the patient 104, the user 122, the computer 106, or combinations thereof. The input device 302 may be an audio input device, a tactile input device, a memory storage device, any now known or later developed input device, or combinations thereof. In one example, the input device 302 is a microphone. In another example, the input device 302 is a keyboard, mouse, trackball, touch pad or other pointer control. In another example, the input device 302 is a memory storage device, such as a hard disk drive, compact disc, digital video disc, flash memory, random access memory, or combinations thereof. In yet another example, the input device 302 is the computer 106.

In one embodiment, the input device 302 is operative to receive input for computing one or more imaging parameter values from a parameter-based analysis of one or more physiological characteristics of a patient 104 or from the results of a direct physiological measurement. For example, the input device 302 may be a keyboard where a user 122 inputs one or more physiological characteristics relating to the patient 104 including, but not limited to, heart rate, blood pressure, age, weight, race, or sex. As an alternative example, the input device 302 may be a compact disc that contains a dataset of one or more physiological characteristics of the patient 104. In yet a further example, the input device 302 is the computer 106, which communicates one or more physiological characteristics of the patient 104 to the computer 108 over a wired connection, a wireless connection, or combinations thereof.

The input interface 304 coupled with the input device 302 is operative to receive the input collected by the input device 302. The input interface 302 may be a wired interface, such as PS/2, USB, Ethernet, IDE/ATA, SCSI, SATA, or IEEE 1394, a wireless interface, such as 802.11 a/b/g, Bluetooth, RF, infrared, an audio interface, such as stereo, S/PDIF, AES/EBU, or combinations thereof. In one embodiment, the input interface 304 is a PS/2 interface coupled with the input device 302, which is a keyboard. In another embodiment, the input interface 304 is an IDE/ATA interface and the input device 302 is a hard drive. In yet a further embodiment, the input interface 304 is an IDE/ATA interface and the input device 302 is a compact disc. In another embodiment, the input interface 304 is an Ethernet interface, and the input device 302 is the computer 106.

The processor 306 is operative to process the information collected by the input device 302. The processor 306 may be a general processor, a data signal processor, graphics card, graphics chip, personal computer, motherboard, memories, buffers, scan converters, filters, interpolators, field programmable gate array, application-specific integrated circuit, analog circuits, digital circuits, combinations thereof, or any other now known or later developed processor. Alternatively, or in addition, the processor 206 is software written in a computer programming language, such as BASIC, C, Dylan, Euphoria, ASP, C++, Java, Python, PHP, Javascript, any now known or later developed computer programming language, or combinations thereof.

In one embodiment, the processor 306 receives one or more physiological characteristics from the computer 106 and communicates with the storage device 308 to store them for later retrieval. In another embodiment, the processor 306 receives data from the input device 302 and calculates one or more imaging parameter values. Calculating one or more imaging parameter values from the one or more physiological characteristics may include the use of a look-up table, a neural network, an expert system, or combinations thereof.

In calculating one or more imaging parameter values, the processor 306 communicates with the imaging parameters database 314. Where the computer 108 implements a look-up table to correlate one or more imaging parameter values with one or more physiological characteristics, the imaging parameter database 314 contains one or more tables that describe the relationship between imaging parameter values and physiological characteristics.

For example, the imaging parameter database 314 may contain a table for the imaging parameter values of angiographic computed tomography. In this example, the rows of the table could represent the age of a person, increasing in value from top to bottom, and the columns could represent blood flow velocity, increasing in value from left to right. Each of the fields where the rows and columns intersect would then represent an imaging parameter value, such as the time delay previously discussed, framerate, the number of projection images to acquire, the maximum amount of contrast to use, the minimum amount of contrast to use, other now known or later developed imaging parameters, or combinations thereof. Using the patient's 104 age and the patient's blood flow velocity as input values for the imaging parameter database 314, the processor 306 could then retrieve one or more imaging parameter values for the inputted age and blood flow velocity.

In another embodiment, the imaging parameter database 314 is implemented as multiple databases, wherein each database represents an imaging modality. In this embodiment, there may be a separate database for traditional angiography and a separate database for angiographic computed tomography. Each of the separate databases then implements one or more tables, wherein each table represents a distinct imaging parameter. For example, the tables in the database for traditional angiography may include the number of projection images to record, the framerate for a set of projection images, the amount of contrast to use (minimum or maximum), the time delay between when the patient is injected with contrast and the time to begin recording projection images of the region of interest, or combinations thereof. Accordingly, using nesting, two-dimensional or multi-dimensional tables, sub-tables, multiple databases, or combinations thereof, the computer 108 can implement the imaging parameter database 314 as a look-up table that allows for relatively fast retrieval of one or more imaging parameter values for one or more imaging modalities given one or more physiological characteristics.

In yet another embodiment, the processor 306 includes software that allows the user 122 to input the imaging parameter values using input device 302 where one or more imaging parameter values are not in the look-up table given an input of one or more physiological characteristics. Alternatively, or in addition, the processor 306 communicates with a central repository, such as over a Local Area Network, a Wide Area Network, or combinations thereof, to update the look-up table for the missing one or more imaging parameter values.

Alternatively, or in addition to implementing a look-up table, the computer 108 may use the imaging parameter database 314 as part of a neural network or expert system, as previously discussed above. In one embodiment where the computer 108 is implemented as an expert system, the imaging parameter database 314 is pre-programmed with facts and rules relating to imaging parameter values and physiological characteristics that allow the processor 306 to derive one or more imaging parameter values for one or more physiological characteristics entered as input from the computer 106, the user 122, or combinations thereof.

For example, the imaging parameter database 314 may be populated with a set facts relating to one or more imaging modalities, such as the number and types of imaging parameters used by the one or more imaging modalities, and a set of rules establishing a relationship between the imaging parameter values of the imaging modalities and one or more physiological characteristics that are possible for a patient. The rules of the imaging parameter database 314 may be goal driven using backward chaining to test whether some hypothesis is true, or data driven, using forward chaining to draw new conclusions from existing data, or combinations thereof. In this embodiment, the processor 306 communicates with the imaging parameter database 314 to derive one or more imaging parameter values using one or more physiological characteristics from the computer 106, the user 122, or combinations thereof, as input to the imaging parameter database 314.

Alternatively, or in addition, the expert system implemented by the processor 306, may include other computers, processors, databases, or combinations thereof, that are used to derive one or more imaging parameter values from one or more physiological characteristics. For example, the computer 108 may use one or more processors as part of the expert system used to derive imaging parameter values, or the computer 108 may be connected to one or more computers using a wired connection, wireless connection, or combinations thereof, as part of an expert system.

The storage device 308 is operative to store input received from the input device 302, data processed by the processor 306, data processed by the graphics controller 310, or combinations thereof. The storage device is also operative to store data relating to the imaging parameter database 314. The storage device 308 may be random access memory, cache memory, dynamic random access memory, static random access memory, flash memory, virtual memory, video memory, magnetic memory, optical memory, any known or later developed memory technology, or combinations thereof. In one embodiment, the storage device 308 is a hard drive. In another embodiment, the memory storage device 308 is a DVD+RW. In a further embodiment, the storage device 308 is a secure digital (SD) card, or other now known or later developed data storage device. The storage device 308 is further operative to allow access to stored data by one or more devices including, but not limited to, the processor 306, the graphics controller 310, the output device 314, one or more devices of the system 102, or combinations thereof.

The graphics controller 310 is operative to control the display of data on the output device 314 coupled with the processor 306. In one embodiment, the graphics controller 310 is operative to control the display of one or more projection images acquired by the X-ray device 116. In another embodiment, the graphics controller 310 is configured to control the display of one or more imaging parameter values calculated by the processor 306. In one embodiment, the graphics controller 310 is a processor. In another embodiment, the graphics controller 310 is software written in a computer programming language, such as BASIC, C, Dylan, Euphoria, ASP, C++, Java, Python, PHP, Javascript, any now known or later developed computer programming language, or combinations thereof.

The output interface 312 facilitates the output of data by the processor 306, the graphics controller 310, any other device coupled with the processor 306, or combinations thereof to the output device 314. The output interface 312 may be a wired interface, such as PS/2, USB, Ethernet, IDE/ATA, SCSI, SATA, IEEE 1394, VGA, DVI, or HDMI, a wireless interface, such as 802.11 a/b/g/n, Bluetooth, RF, infrared, an audio interface, such as stereo, S/PDIF, AES/EBU, EIAJ optical, or combinations thereof.

The output device 314 outputs data processed by the processor 306, the graphics controller 310, or combinations thereof, communicated through the output interface 312. The data output by the output device 314 may text, graphics, or combinations thereof. The output device 314 may be a display device such as a monitor, CRT, LCD, plasma screen, flat-panel, projector are other now known or later developed display device, a printing device, such as a laserjet printer, a color printer, any other now known or later developed printing device, a storage device, another computer, or combinations thereof. The output device 314 can also be the output device 114. The output device 314 can also be any other device of the system 102, including, but not limited to, the computer 106, the controller 110, the X-ray device 116, the perfusion evaluation computer 112, the output device 114, or combinations thereof.

The data output by the output device 314 may include one or more imaging parameter values calculated by the processor 306, one or more imaging parameter values input to the input device 302, one or more projection images output by the X-ray device 116, two-dimensional or otherwise, representative of an region of interest in the patient 104, or combinations thereof. The output device 314 may also output a user interface allowing the patient 104, the user 122, any other device of the system 102, or combinations thereof, to interact with the computer 108.

Figure 4:
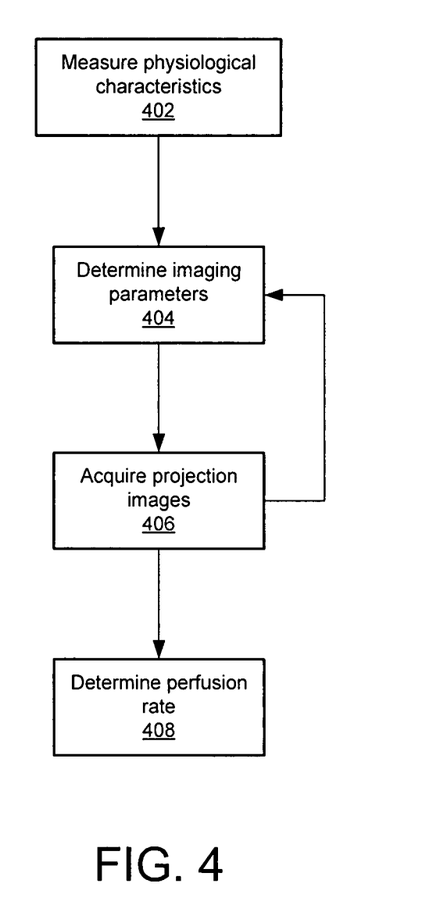
FIG. 4 is a flowchart of one example of obtaining perfusion images based on one or more measured physiological characteristics of a patient.

FIG. 4 is a flowchart of one example of obtaining perfusion images based on one or more measured physiological characteristics of a patient. With reference to FIG. 1, the user 122, the computer 106, or combinations thereof, measure one or more physiological characteristics of a patient 104 (Block 402). The one or more physiological characteristics are then used by a processor to calculate or determine one or more imaging parameter values (Block 404). Using the calculated imaging parameter values, the X-ray device 116 acquires one or more projection images using a selected imaging modality (Block 406). After the one or more projection images are acquired, the controller 110, the user 122, or combinations thereof, may communicate with the computer 108 to calculate additional imaging parameter values for another imaging modality. After the one or more projection images are acquired, a perfusion rate of the region of interest is determined by the perfusion evaluation computer 112, the user 122, or combinations thereof (Block 408).

Figure 5:
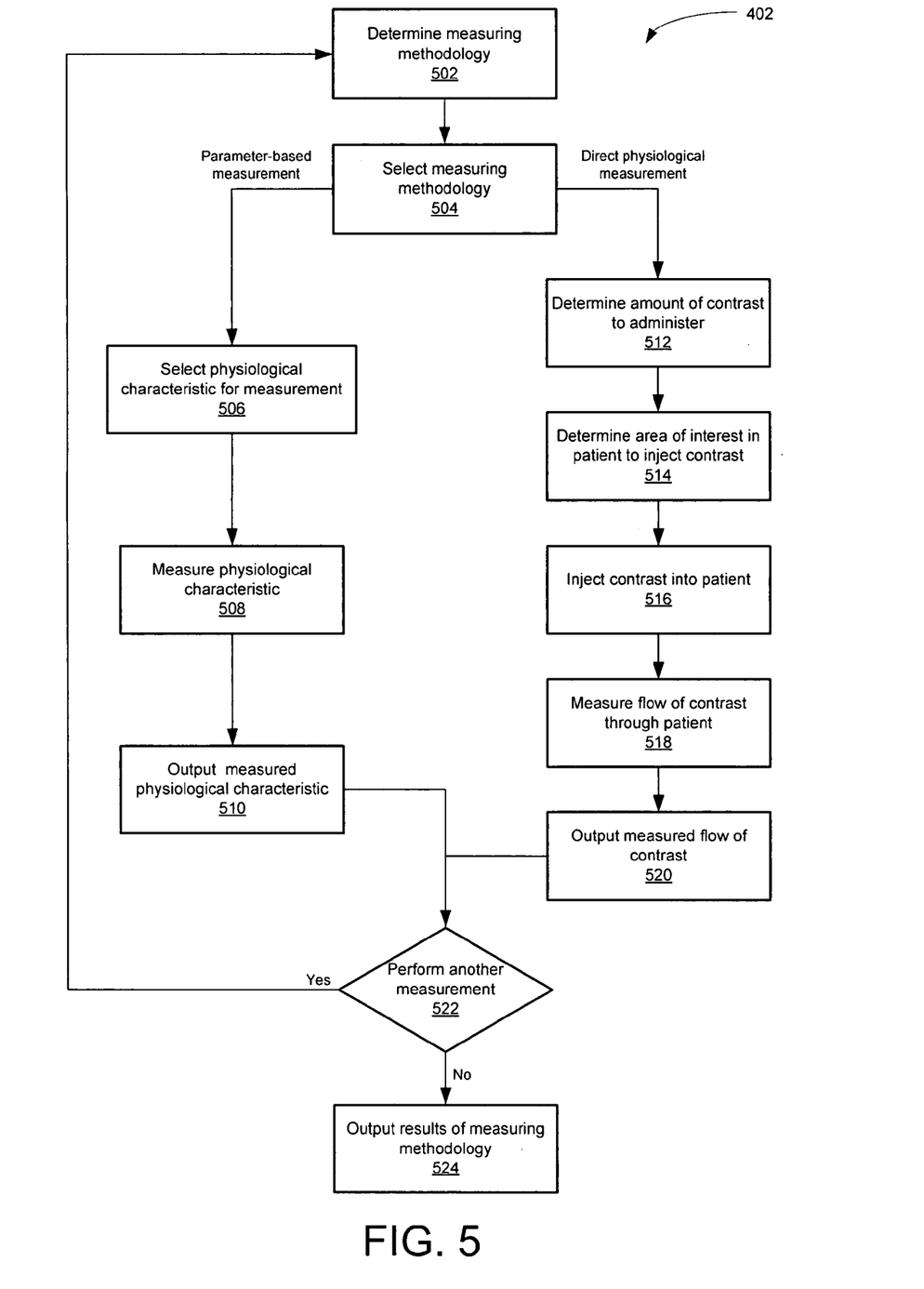
FIG. 5 is a flowchart of one example of measuring one or more physiological characteristics of a patient.

FIG. 5 is a flowchart of one example of measuring one or more physiological characteristics of a patient. Initially, the user 122, the computer 106, or combinations thereof, determine a measuring methodology for measuring one or more physiological characteristics of a patient 104 (Block 502). For example, the user 122, the computer 106, or combinations thereof, may determine that the patient 104 should first undergo a parameter-based measurement, and then later, a direct physiological measurement. Alternatively, the user 122, the computer 106, or combinations thereof, may determine that one measuring methodology is preferable over another, such as preferring a parameter-based measurement where the patient 104 is unable or unwilling to undergo a direct physiological measurement. Determining which measuring methodology to perform may include receiving input from the user 122, the patient 104, or combinations thereof, or may include the computer 106 performing calculations on previously provided information.

After determining which measuring methodology to perform, the user 122, the computer 106, or combinations thereof, then selects the measuring methodology to perform (Block 504). In one embodiment, the computer 106 selects a parameter-based measurement for determining one or more physiological characteristics of a patient. In this embodiment, the user 122, the computer 106, or combinations thereof, first selects one or more physiological characteristics to measure (Block 506). For example, the computer 106 may communicate with the computer 108 to determine which physiological characteristics are needed to compute one or more imaging parameter values. Alternatively, the computer 106 may be preprogrammed with a set of physiological characteristics to measure as a default set of physiological characteristics. In yet another embodiment, the user 122 may provide the computer 106 with a list of physiological characteristics to measure and an order in which to measure each physiological characteristic. After selecting the physiological characteristic to measure, the computer 106 then measures the selected physiological characteristic (Block 508). The computer 106 may then select and measure additional physiological characteristics. After measuring the physiological characteristic, the data representing the physiological characteristic is then output, such as by being stored in the storage device 208 or output to the output device 114 (Block 510). The computer 106 may then prompt the user 122 whether to perform another measurement, such as by selecting an additional measuring methodology, or by selecting an additional physiological characteristic to measure (Block 522).

Alternatively, or in addition to performing a parameter-based measurement, the computer 106, the user 122, or combinations thereof, may select to perform a direct physiological measurement. In one embodiment, performing a direct physiological measurement on the patient 104 includes injecting the patient 104 with a contrast agent (test bolus). In this embodiment, the computer 106 initially determines the amount of contrast to administer to the patient 104 (Block 512). The user 122 could also determine the amount of contrast to administer to the patient 104. The amount of contrast agent to inject in the patient 104 may be specified according to a previously established protocol, the patient's 104 medical history, or any other measure for determining an amount of contrast to inject into a patient, or combinations thereof.

After the amount of contrast agent is determined, an region of interest in the patient 104 is selected in which to inject the contrast agent (Block 514). The selected region of interest may be the same, or different from, the region of interest in the patient 104 for which the rate of perfusion is determined. For example, where there is a stenosis in a coronary artery, the selected region of interest to inject the contrast agent may include the lower extremities of the patient 104. However, in this example, the selected region of interest to inject the contrast agent may include an region of interest near the constricted coronary artery. Criteria for selecting the region of interest in which to inject the contrast agent may be based on a predefined protocol programmed into the computer 106, a discretionary selection by the user 122, a selection based on the health of the patient 104, any other criteria used for selecting an area in which to perform an injection, or combinations thereof.

Following a determination of the region of interest in which to inject the contrast agent, the contrast agent is then injected into the patient 104 (Block 516). The injection may be performed by the computer 106, by a device coupled with the computer 106, by the user 122, or combinations thereof.

The contrast agent injected into the region of interest is then monitored or measured (Block 518). As previously described above, monitoring of the contrast agent through the injected region of interest may include acquiring one or more projection images of the injected region of interest with the X-ray device 116, evaluating TIMI flow grades of the injected region of interest, monitoring the time of perfusion of the injected region of interest, counting the number of projection images acquired by the X-ray device 116, any other type of monitoring, or combinations thereof. The measurements derived from monitoring the flow of contrast agent through the injected region of interest include can be further used to generate data representative of a time attenuation curve or to determine the blood flow velocity of the injected region of interest. The measurements of the flow of the contrast agent through the injected region of interest are then output, such as by being stored in the storage device 208 or output to the output device 214 (Block 520).

After the user 122, the computer 106, or combinations thereof, have finished determining one or more physiological characteristics and does not select to perform another measurement, the results of the one or more measuring methodologies are output (Block 524). In one embodiment, the results of the one or more measuring methodologies are buffered stored in the computer 106, and then output to the output device 214. In an alternative embodiment, the results of the one or more measuring methodologies are transferred from the storage device 208 to the output device 214, from the output device 214 to the storage device 208, or combinations thereof.

Figure 6:
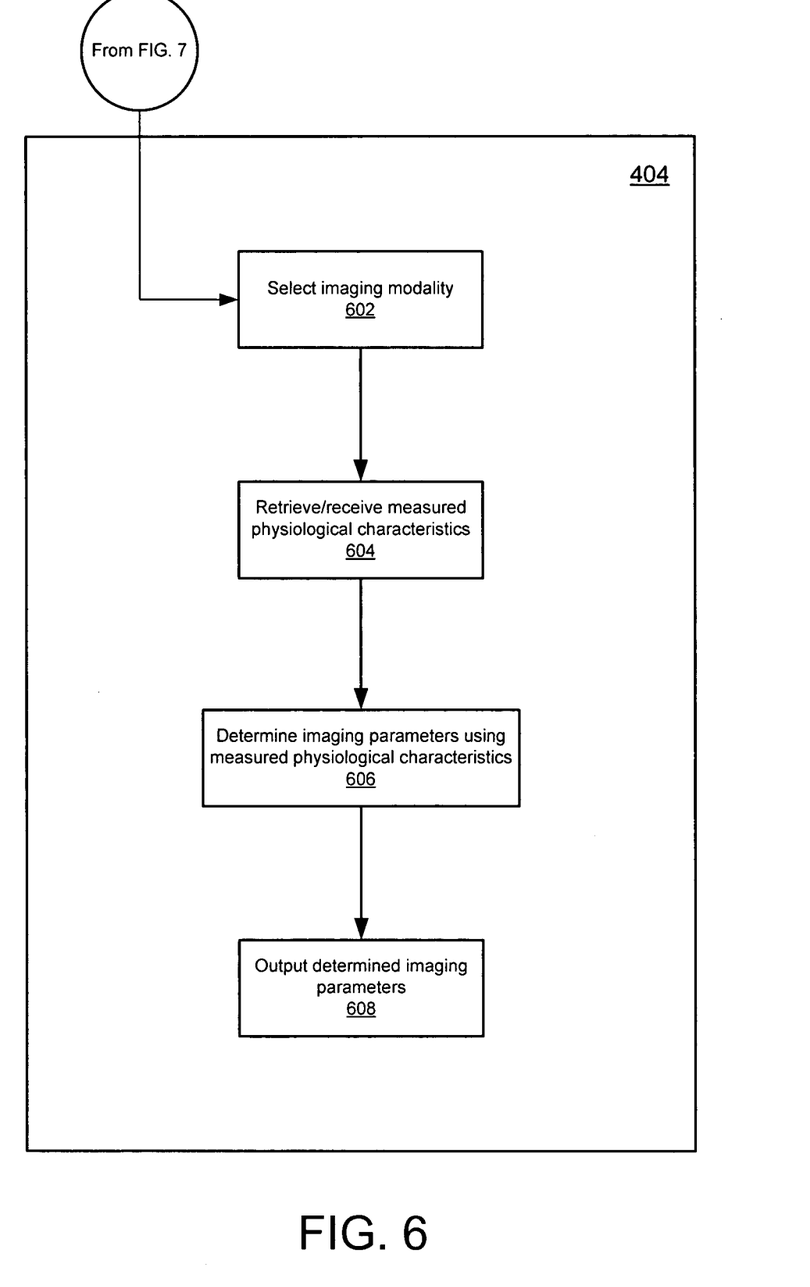
FIG. 6 is a flowchart of one example of determining imaging parameter values of one or more imaging modalities based on measured physiological characteristics of a patient.

Referring now to FIG. 6 with reference to FIG. 1 and FIG. 3, is a flowchart of one example of determining imaging parameter values of one or more imaging modalities based on measured physiological characteristics of a patient 104. In one embodiment, the computer 108, the user 122, or combinations thereof, selects an imaging modality for the controller 110 to use in acquiring one or more projection images of an region of interest in the patient 104 (Block 602). Examples of imaging modalities include traditional angiography, angiographic computed tomography, any other type of angiographic imaging modality, or combinations thereof. After selecting an imaging modality, the computer 108 retrieves or receives one or more physiological characteristics measured by the computer 106. In one embodiment, the physiological characteristics are sent as output to the computer 108 after being determined. In another embodiment, the computer 108 requests the computer 106 to transmit or send one or more physiological characteristics.

Using the selected imaging modality and one or more measured physiological characteristics, the computer 108 determines one or more imaging parameter values for the selected imaging modality (Block 606). As previously discussed above, the computer 108 may determine one or more imaging parameter values using a look-up table, a neural network, an expert system, or combinations thereof. In an alternative embodiment, the computer 108 determines one or more imaging parameter values for each of the imaging modalities supported by the controller 110 and the X-ray device 116. For example, the computer 108 may determine one or more imaging parameter values for traditional angiography and for angiographic computed tomography. The determined one or more imaging parameter values are then output by the computer 108 (Block 608). The output of the determined one or more imaging parameter values may include storing the one or more imaging parameter values on the storage device 308, displaying the one or more imaging parameter values on a display device, transmitting the one or more imaging parameter values to the controller 110, any other type of output, or combinations thereof.

Figure 7:
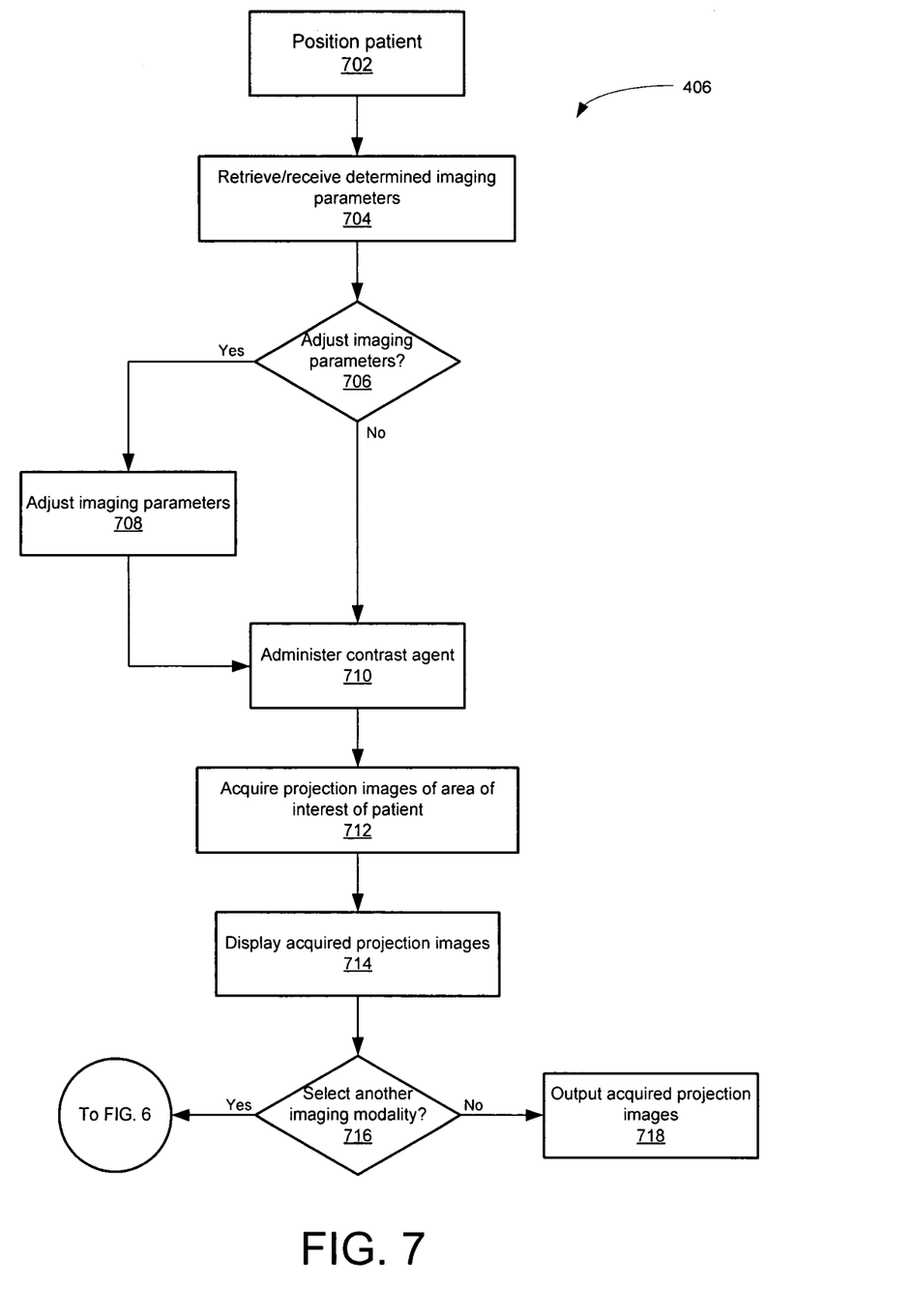
FIG. 7 is a flowchart of one example of acquiring projection images based on the measured one or more physiological characteristics of a patient.

With reference to FIG. 1, FIG. 7 is a flowchart of one example of acquiring projection images of an region of interest in the patient 104 using the one or more determined imaging parameter values. According to the embodiment shown in FIG. 7, the user 122, the controller 110, or combinations thereof, initially positions the patient 104 on the X-ray device 116 (Block 702). Positioning the patient 104 may include positioning an region of interest of the patient 104 between the X-ray source 118 and the X-ray detector 120. Alternatively, where the region of interest was acquired by the X-ray device 116 in performing a direct physiological measurement, the user 122, the controller 110, or combinations thereof, may not position the patient 104.

After the patient 104 is positioned, or while the patient 104 is being positioned, the controller 110 retrieves or receives the determined one or more imaging parameter values from the computer 108 for a selected imaging modality. Alternatively, the controller 110 retrieves or receives one or more imaging parameter values determined by the computer 108 for each of the imaging parameter values performable by the controller 110 and the X-ray device 116. In one embodiment, the controller 110 is configured to allow the user 122 to select which imaging modality to use with the X-ray device 116, which imaging parameter values to use with one or more imaging modalities, or combinations thereof.

When the controller 110 has the imaging parameter values, a determination is made whether to adjust one or more imaging parameter values (Block 706). The determination may be made by the controller 110 based on the imaging modality selected by the user 122. Alternatively, the controller 110 may prompt the user 122 to adjust one or more imaging parameter values. Adjusting one or more imaging parameter values includes, but is not limited to, increasing or decreasing the value of an imaging parameter, adding or removing an imaging parameter, re-calculating an imaging parameter value, any other type of adjustment, or combinations thereof. For example, the user 122, the controller 110, or combinations thereof, may determine to increase the number of projection images acquired by the X-ray device 116. Alternatively, the user 122, the controller 110, or combinations thereof, may determine to increase the framerate of the projection images acquired by the X-ray device 116. In yet a further example, the user 122, the controller 110, or combinations thereof, may determine to increase or decrease the time delay determined by the computer 108. If a determination is made to adjust one or more imaging parameter values, the user 122, the controller 110, or combinations thereof, adjusts the one or more imaging parameter values (Block 708).

Whether the user 122, the controller 110, or combinations thereof, decide to adjust one or more imaging parameter values, the user 122 then administers the contrast agent to the patient 104 (Block 710). In one embodiment, the user 122 administers the contrast agent to the patient 104 by injecting the contrast agent near the region of interest. After the contrast agent has been administered to the patient 104, one or more projection images 712 are acquired of the injected region of interest using the one or more imaging parameter values determined by the computer 108. As discussed above, the one or more imaging parameter values used to acquire one or more projection images of the region of interest may have been adjusted. As the X-ray device 116 is acquiring the one or more projection images of the region of interest of the patient 104, the one or more projection images are displayed (Block 714). In one embodiment, the one or more projection images being acquired are displayed on the output device 114 coupled with the controller 110.

After the X-ray device 116 has acquired one or more projection images of the region of interest according to one or more imaging parameter values, the controller 110, the user 122, or combinations thereof, makes a determination whether to acquire another set of one or more projection images using an alternative imaging modality (Block 716). For example, where one or more projection images of the region of interest were acquired using traditional angiography, the controller 110, the user 122, or combinations thereof, may decide to acquire one or more projection images using angiographic computed tomography.

Where the controller 110, the user 122, or combinations thereof, decide to acquire one or more projection images using an alternate imaging modality, the controller 110, the user 122, or combinations thereof, selects an alternate imaging modality (Block 602). Alternatively, the controller 110, the user 122, or combinations thereof, may decide to acquire another set of one or more projection images of the region of interest using the same imaging modality. For example, the controller 110, the user 122, or combinations thereof, may decide to acquire one or more projection images using the same imaging modality but with a different set of one or more imaging parameter values. In this example, the controller 110, the user 122, or combinations thereof, would be given the opportunity to adjust one or more imaging parameter values before acquiring one or more projection images of the region of interest using the same imaging modality. However, the controller 110, the user 122, or combinations thereof, may determine to acquire another set of one or more projection images using the same imaging modality with the same one or more imaging parameter values.

After the X-ray device 116 has acquired one or more projection images of the region of interest, the one or more projection images are output to the output device 114, the perfusion evaluation computer 112, or combinations thereof (Block 718). Alternatively, each time the X-ray device 116 has finished acquiring one or more projection images for a selected imaging modality, the one or more projection images are output to the output device 114. For example, where a first set of one or more projection images are acquired using the X-ray device 116, and a second set of one or more projection images are to be acquired, the first set of one or more projection images are output to the output device 114 before the second set of one or more projection images are acquired. However, it is also possible that the first set of projection images is buffered stored while the second set of projection images are acquired. Outputting to the output device 114 includes, but is not limited to, displaying one or more projection images, storing one or more projection images, printing one or more projection images, any other now known or later developed method of output, or combinations thereof. Outputting one or more projection images of the region of interest also includes outputting data representative of one or more projection images of the region of interest.

Figure 8:
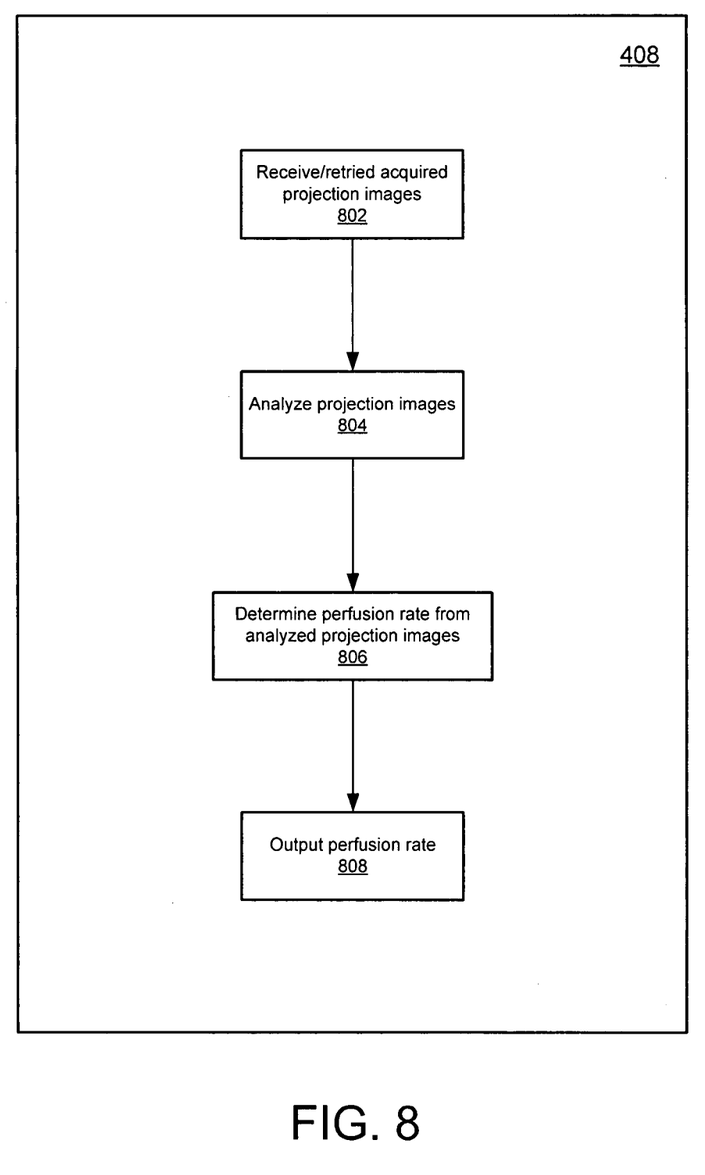
FIG. 8 is a flowchart of one example of determining the perfusion rate of an region of interest in the patient based on acquired one or more projection images.

With reference to FIG. 1, FIG. 8 is a flowchart of one example of determining the perfusion rate of an region of interest in the patient 104 based on acquired one or more projection images. As previously described above, the evaluation of the perfusion rate of the region of interest may be performed by the user 122, the perfusion evaluation computer 112, or combinations thereof. In one embodiment, data representative of the one or more projection images is received by the perfusion evaluation computer 112 (Block 802). In another embodiment, the user 122 views the one or more projection images on the output device 114. An analysis of the one or more projection images is then performed by the user 122, the perfusion evaluation computer 122, or combinations thereof (Block 804). In one embodiment, the analysis of the one or more projection images includes assigning TIMI flow grades to one or more projection images. In another embodiment, the analysis of the one or more projection images includes evaluating one or more pixel values for one or more pixels. In yet a further embodiment, analysis of the one or more projection images includes assigning a reference image for the one or more projection images and comparing each of the one or more projection images to the reference image. Analyzing the one or more projection images may also include outputting data to the output device 114, or communicating with one or more devices in the system 102.

After the analysis of the one or more projection images is complete, a perfusion rate of the region of interest represented by the one or more projection images is determined (Block 806). As discussed above with reference to FIG. 1, the perfusion rate of the region of interest may be determined by the user 122, the perfusion evaluation computer 112, any other devices or components coupled with the system 102, or combinations thereof. In one embodiment, the perfusion rate of the region of interest is output to the output device 114. For example, where the output device 114 is a printer, the perfusion rate of the region of interest over the period in which the one or more projection images were acquired is printed as a time-series graph. Alternatively, where the output device 114 is a display device, the perfusion rate of the region of interest is displayed for viewing by the user 122. In yet a further embodiment, the perfusion rate of the region of interest is output to the computer 106, the computer 108, the controller 110, any other devices coupled with the system 102, or combinations thereof.

The perfusion rate of the region of interest may be used to evaluate the performance of an intervention, or to further determine the location of a stenosis or blockage in the region of interest. For example, where an intervention is performed on the patient 104, the perfusion rate of the region of interest can be used to determine whether the intervention was successful. In this example, if the perfusion rate of the region of interest is greater after the intervention is performed, this would indicate to the user 122 that the intervention was most likely successful. Similarly, if the perfusion rate of the region of interest remains unchanged before an intervention and after the intervention, this would indicate to the user 122 that the intervention was most likely unsuccessful. In this manner, the user 122, the computer 106, the computer 108, the controller 110, the perfusion evaluation computer 112, or combinations thereof, can adjust one or more imaging parameter values to further locate a stenosis or blockage.

It is intended that the foregoing detailed description be understood as an illustration of selected forms that the invention can take and not as a definition of the invention. It is only the following claims, including all equivalents, that are intended to define the scope of this invention.

We claim:

1. A system for obtaining perfusion images, the system comprising:
    a first processor configured to determine a physiological characteristic of a patient;
    a second processor configured to receive the determined physiological characteristic of the patient, and further configured to determine an imaging parameter value of an imaging modality based on the determined physiological characteristic;
    a memory configured to store the imaging parameter value;
    an X-ray device configured to acquire a projection image representative of a region of interest of the patient using the stored imaging parameter value of the imaging modality determined based on the measured physiological characteristic;
    a third processor configured to receive the acquired projection image and further configured to determine a perfusion rate of the region of interest based on the acquired projection image; and
    an output device configured to output the determined perfusion rate of the region of interest.

2. The system of claim 1 where the first processor is configured to compute the physiological characteristic of the patient based on monitoring the flow of a contrast bolus administered to the patient.

3. The system of claim 1 where the second processor is configured to determine the imaging parameter value by correlating a predetermined set of values with the measured physiological characteristic.

4. The system of claim 1 where the second processor is an expert system that uses the measured physiological characteristic as an input to determine the imaging parameter value.

5. The system of claim 1 where the imaging parameter value is a time delay between a time in which the patient is injected with a contrast agent and a time in which the X-ray device acquires the projection image.

6. The system of claim 1 where the imaging parameter value is a number of projection images of the region of interest of the patient to be acquired during a predetermined time interval.

7. The system of claim 1 where the imaging modality is angiographic computed tomography.

8. The system of claim 1 where the third processor is further configured to compute the perfusion rate of the region of interest based on a comparison of myocardial blush represented in a projection image for each projection image in a set of acquired projection images representative of the region of interest.

9. The system of claim 1 where the output device is a display device operable to display the perfusion rate of the region of interest.

10. The system of claim 1 where the first processor, the second processor, and the third processor are a same processor.

11. The system of claim 1 where the first processor, the second processor, and the third processor are different processors.

12. The system of claim 1 where the first processor is configured to determine the physiological characteristic of the patient using a parameter-based analysis of the patient.

13. The system of claim 12 where the first processor is configured to compute a blood flow velocity of the circulatory system of the patient.

14. A method for obtaining perfusion information, the method comprising:
    measuring, with a first processor, at least one physiological characteristic of a patient;
    determining, with a second processor, at least one imaging parameter value of at least one imaging modality as a function of the at least one measured physiological characteristic;
    storing, with a memory, the at least one imaging parameter value;
    acquiring, with an imaging device, at least one projection image representative of a region of interest of the patient using the at least one stored imaging parameter value;
    determining, with a third processor, a perfusion rate of the region of interest based on the at least one acquired projection image; and
    outputting the perfusion rate of the region of interest to an output device.

15. The method of claim 14 where determining the at least one imaging parameter value comprises determining the at least one imaging parameter value by correlating a predetermined set of values with the at least one measured physiological characteristic.

16. The method of claim 14 where the at least one imaging parameter value is a time delay between a time in which the patient is injected with a contrast agent and a time in which the at least one projection image is acquired.

17. The method of claim 14 where the at least one imaging modality is angiographic computed tomography.

18. The method of claim 14 where determining the perfusion rate of the region of interest comprises computing the perfusion rate of the region of interest based on a comparison of myocardial blush represented in a projection image for each projection image in a set of acquired projection images representative of the region of interest.

19. The method of claim 14 where outputting the perfusion rate of the region of interest comprises storing the perfusion rate of the region of interest on a storage device.

20. The method of claim 14 where the first processor, the second processor, and the third processor are a same processor.

21. The method of claim 14 where the first processor, the second processor, and the third processor are different processors.

22. The method of claim 14 where measuring at least one physiological characteristic of the patient comprises conducting a parameter-based analysis of the patient.

23. The method of claim 22 where conducting a parameter-based analysis of the patient comprises computing a blood flow velocity of the circulatory system of the patient.

24. The method of claim 14 where measuring at least one physiological characteristic of the patient comprises conducting a physiological measurement of a contrast bolus administered to the patient.

25. The method of claim 24 where conducting a physiological measurement of a contrast bolus administered to the patient comprises determining the flow of the contrast bolus through the region of interest of the patient.

26. The method of claim 14 where determining the at least one imaging parameter value comprises using the at least one measured physiological characteristic as an input to a computer to compute the least one imaging parameter value.

27. The method of claim 26 where the computer is an expert system.

28. A non-transitory computer-readable medium having computer-executable instructions for obtaining perfusion information, the computer-executable instructions comprising:
    measuring at least one physiological characteristic of a patient;
    determining, with a processor, at least one imaging parameter value of at least one imaging modality as a function of the at least one measured physiological characteristic;
    storing the at least one imaging parameter value;
    acquiring at least one projection image representative of the region of interest of the patient using the at least one stored imaging parameter value;
    determining a perfusion rate of the region of interest based on the at least one acquired projection image; and
    outputting the perfusion rate of the region of interest to an output device.

* * * * *